US008801600B2

(12) United States Patent
Zipper

(10) Patent No.: US 8,801,600 B2
(45) Date of Patent: Aug. 12, 2014

(54) SEXUAL STIMULATION DEVICE USING LIGHT THERAPY

(71) Applicant: Ralph Zipper, Melbourne, FL (US)

(72) Inventor: Ralph Zipper, Melbourne, FL (US)

( * ) Notice: Subject to any disclaimer, the term of this patent is extended or adjusted under 35 U.S.C. 154(b) by 0 days.

(21) Appl. No.: 13/828,445

(22) Filed: Mar. 14, 2013

(65) Prior Publication Data

US 2013/0261385 A1 Oct. 3, 2013

Related U.S. Application Data

(60) Provisional application No. 61/610,899, filed on Mar. 14, 2012.

(51) Int. Cl.
*A61F 5/00* (2006.01)
(52) U.S. Cl.
USPC .......................................................... 600/38
(58) Field of Classification Search
USPC ......... 600/38–40; 601/46, 134, 70, 80, 99, 15
See application file for complete search history.

(56) References Cited

U.S. PATENT DOCUMENTS

| 4,722,326 | A | | 2/1988 | Ruderian | |
|---|---|---|---|---|---|
| 5,067,480 | A | | 11/1991 | Woog et al. | |
| 5,336,159 | A | * | 8/1994 | Cheng | 601/15 |
| 5,925,002 | A | | 7/1999 | Wollman | |
| 6,110,102 | A | | 8/2000 | Harrison | |
| 6,190,307 | B1 | | 2/2001 | Tsai | |
| 6,932,779 | B2 | * | 8/2005 | Kasai | 601/99 |
| 7,341,566 | B2 | | 3/2008 | Nan | |
| 7,419,475 | B2 | | 9/2008 | Ferber et al. | |
| 7,749,178 | B2 | | 7/2010 | Imboden et al. | |
| 7,815,582 | B2 | | 10/2010 | Imboden et al. | |
| 2003/0199946 | A1 | | 10/2003 | Gutwein | |
| 2003/0232303 | A1 | | 12/2003 | Black | |
| 2005/0113725 | A1 | * | 5/2005 | Masuda | 601/72 |
| 2005/0197982 | A1 | | 8/2005 | Fox | |
| 2006/0069330 | A1 | | 3/2006 | Nan | |

(Continued)

FOREIGN PATENT DOCUMENTS

WO  WO2011159906  12/2011

OTHER PUBLICATIONS

International Search Authority, International Search Report and Written Opinion of the International Searching Authority, date of mailing Jun. 11, 2013, ISA/US, Alexandria, Virginia, United States.

(Continued)

*Primary Examiner* — Christine Matthews
(74) *Attorney, Agent, or Firm* — Stephen C. Thomas

(57) ABSTRACT

A sexual stimulation apparatus which may comprise a plurality of light sources for photostimulation and microbe reduction of the vagina, clitoris, or both; a plurality of vibrators for mechanical stimulation of the vagina, clitoris, or both; a plurality of modes of operation for achieving improved sexual stimulation in a user; a handle for ease of operation; a controller and programmable memory for containing modes of operation and driving the light sources and vibrators of the invention; a vaginal finger; a clitoral finger; a handle for ease of use; a keypad for user entry of commands; a charging and programming port; and a power source which may be a rechargeable battery which may be rechargeable by direct, inductive or other means; and a handle for ease of operation. The invention also comprises a flexible covering that provides smooth sliding engagement with the vagina and clitoris of a user.

28 Claims, 8 Drawing Sheets

(56) References Cited

U.S. PATENT DOCUMENTS

| | | |
|---|---|---|
| 2006/0084837 A1 | 4/2006 | Klearman |
| 2006/0135892 A1 | 6/2006 | Nan |
| 2007/0149903 A1 | 6/2007 | Nan |
| 2008/0071138 A1 | 3/2008 | Mertens et al. |
| 2008/0091127 A1 | 4/2008 | Nan |
| 2008/0119767 A1* | 5/2008 | Berry et al. ............. 601/46 |
| 2008/0139980 A1 | 6/2008 | Fladl |
| 2008/0306417 A1 | 12/2008 | Imboden et al. |
| 2009/0093673 A1 | 4/2009 | Lee |
| 2009/0099413 A1 | 4/2009 | Kobashikawa |
| 2010/0174136 A1 | 7/2010 | Shim |
| 2010/0268021 A1* | 10/2010 | Standfest et al. ............. 600/38 |
| 2011/0034837 A1 | 2/2011 | Lee |
| 2011/0071445 A1 | 3/2011 | Imboden et al. |
| 2011/0098613 A1 | 4/2011 | Thomas et al. |
| 2011/0105837 A1 | 5/2011 | Lee |
| 2011/0124959 A1 | 5/2011 | Murison |
| 2011/0224584 A1 | 9/2011 | Pryor et al. |
| 2011/0319707 A1 | 12/2011 | Mertens et al. |
| 2012/0215141 A1 | 8/2012 | Peddicord |
| 2012/0220907 A1 | 8/2012 | Zinn |
| 2012/0291208 A1 | 11/2012 | Edwards |

OTHER PUBLICATIONS

International Preliminary Report on Patentability, date of mailing Jan. 28, 2014, ISA/US, Alexandria, Virginia, United States.

* cited by examiner

Fig. 9

| Exemplary Vibration Patterns | |
|---|---|
| Description | Vibrator State |
| Constant ("C") | Vibrator on at constant power level |
| In Phase Pulse ("IPP") | Vibrator on for 0.4 seconds and off for 0.4 seconds |
| Out of Phase Pulse ("OPP") | Vibrator off for 0.4 seconds and on for 0.4 seconds |
| In Phase Wave ("IPW") | Vibrator intensity modulated as a sine wave with a 1.2 second period in phase as between vaginal and clitoral vibrators |
| Out of Phase Wave ("OPW") | Vibrator intensity modulated as a sine wave with a 1.2 second period out of phase as between vaginal and clitoral vibrators |
| Fast Pulse ("FP") | Vibrator on for 0.2 seconds and off for 0.2 seconds |

Fig. 10

| Exemplary Mode of Operation | | | | | | |
|---|---|---|---|---|---|---|
| Elapsed Time (sec) | | 0-60 | 60-180 | 180-300 | 300-480 | 480- |
| Vaginal Finger | LED Pattern | PW1 | PW2 | PW3 | PW4 | PW4 |
| | Vibrator Pattern and Intensity | C LOW | C MEDIUM | IPW MEDIUM | IPW HIGH | C MEDIUM |
| Clitoral Finger | LED Pattern | LSO 1 | LSO 2 | LSO 3 | LSO 4&5 | LSO 4&5 |
| | Vibrator Pattern and Intensity | C LOW | C MEDIUM | OPW MEDIUM | OPW HIGH | C MEDIUM |

Fig. 11

SEXUAL STIMULATION DEVICE USING LIGHT THERAPY

CROSS REFERENCE TO RELATED APPLICATIONS

This application claims the benefit of provisional patent application Ser. No. 61/610,899 filed with the United States Patent and Trademark Office on Mar. 14, 2012, which is herein incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The improved sexual stimulation device of the invention relates generally to the field of female sexual stimulation devices, more specifically, handheld sexual stimulation devices using vibration techniques in order to achieve stimulation.

2. Background Art

A variety of handheld sexual stimulating devices have been described in the art, many of which are commercially available, and some of which have been the subject of patents. The devices of the prior art may combine mechanical vibration with other stimulation, such as heat. For example, a vibratory therapy device comprising a lightweight portable housing encasing a heater/vibrator assembly for imparting vibratory action to a massaging head, together with heated airflow, is described in U.S. Pat. No. 4,722,326. The device includes a plurality of interchangeable massage heads having different surface textures or configurations.

An electric vibrating or massaging device having a plurality of detachable attachments for use in marital or sexual orgasmic therapy is also taught in U.S. Pat. No. 5,067,480. This device includes a stimulator that rotationally oscillates through a range of angles for stimulation of appropriate body areas in marital or sexual orgasmic therapy.

None of the aforementioned vibrating or massage devices combine the use of therapeutic light energy for photostimulation and or photobiomodulation and vibration in a single apparatus which provides multiple modes of use including programmable mechanical stimulation and light energy control, multiple frequencies of light energy, a plurality of vibrators or mechanical stimulators and therapeutic light sources which are intended to increase blood flow, improve tissue health, and decrease microbes and therefore improve sexual stimulation and genital health, and numerous pre-programmed modes of operation. "Mechanical stimulation", as used herein, is defined as mechanical manipulation of a body surface that is perceivable by a person and wherein said mechanical manipulation is achieved by any means including but not limited to vibration, sonic pulses, rubbing, tapping, pressure, pressure that varies in intensity, and any other form of mechanical manipulation of surface body tissue in a perceptible manner. "Therapeutic light", as used herein, refers to any light, visible or not visible, that exerts an effect to the biologic or chemical status of the tissue or microbe to which it is applied, with such effect or effects being other than that of the activation or modification photosensitive receptors of the human eye. Examples of therapeutic effects may include but not be limited to alteration is cellular respiration, alteration or activation of enzyme or enzyme pathways, alteration in mitochondrial activity, the production or reduction in adenosine triphosphate or similar molecules, the production or reduction of nitric oxide or similar chemicals, changes in blood pressure, muscle relaxation, muscle contraction, cellular activation, modification of the inflammatory response, modification of the healing response, hastening of microbe activity, alteration of microbe activity, and microbe death. Therapeutic light may be referred to as photostimulation when the effects of said light are stimulating in nature. Therapeutic light may be referred to as photomodulation or photobiomodulation when the effect of said light are other than stimulatory or beyond stimulatory.

Applicant's invention, described and claimed herein, therefore provides a significant improvement and inventive step over the state of the art.

BRIEF SUMMARY OF THE INVENTION

The present invention comprises a system and method that has one or more of the following features and/or steps, which alone or in any combination may comprise patentable subject matter.

In accordance with one embodiment of the improved sexual stimulation device of the invention, the invention is a vibrating stimulator for female use which may incorporate one or more therapeutic light sources and may also incorporate one or more mechanical stimulators in the form of vibrators, which, when applied to the clitoris or vagina, or both, cause increased stimulation and/or therapeutic effect resulting in an enhanced sexual experience for the user. In accordance with an alternate body of the invention, the invention is a stimulator for male use which incorporates a light source for increased stimulation and/or therapeutic effect.

In the prior art female sexual stimulation devices were designed to vibrate and stimulate the nerves of sexually sensitive areas of the female anatomy, for instance the clitoris or Grafenberg Spot (G-spot). Although effective, this method of stimulation typically bypasses or rapidly moves through one of the most important phases of the sexual response cycle which is the arousal phase. This phase, also known as the excitement phase, is characterized by increased blood flow to the clitoris and vagina as well as an increase in muscle tone to the vagina and anus. The present invention may utilize therapeutic light energy to enhance genital blood flow. The ability of specific wavelengths of light to stimulate blood flow through the application of light energy is well established throughout medical literature. The application of light energy to certain parts of the body may improve blood flow and may therefore improve sexual response with or without a partner. Improved blood flow can also extend a woman's sexual lifespan. The apparatus and method of the invention causes greater clitoral swelling and signs of improved genital blood flow, which may result in enhanced or more frequent orgasms (or both). Additionally, the present invention may utilize specific wavelengths of therapeutic light to decrease vaginal and vulvar bacteria and fungi populations. The medical and environmental literature is replete with data demonstrating specific wavelengths of light to be bactericidal, bacteriostatic, fungicidal and fungistatic. The application of such light energy to the vagina, vulva, clitoris, and penis may reduce bacterial and fungal infections that may be caused by the use of stimulating devices or exist unrelated to such.

A preferred embodiment of the invention comprises a handle portion which may house control elements such as buttons, switches and the like, a vaginal finger which may contain at least one vibrator and at least one light source for insertion into the vagina of a female user, and a clitoral finger which may contain at least one vibrator and at least one light source for application to the clitoris of a female user. It is preferred that, when a preferred embodiment of the improved sexual stimulation device of the invention is used in a best mode, the vaginal finger directly applies vibration and light stimulation on or near the Grafenberg Spot, or G-spot, of a female user, and the clitoral finger directly applies vibration and light stimulation on or near the clitoris of a user. In this manner, vibration and light stimulation are directly applied to the areas of the body known to result in maximum arousal and sexual stimulation. The improved sexual stimulation device of the invention may be used in numerous orientations and modes which are limited only by the imagination of the user or the user's partner, and are therefore not to be limited by the best mode described herein. Although the preferred embodiments combine therapeutic wavelengths of light with vibration, other forms of mechanical stimulation such as that used in neck massagers and massaging chairs may also comprise the invention.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating the preferred embodiments of the invention and are not to be construed as limiting the invention. The drawings of the various figures may not be too scale and some features may be exaggerated or minimized in order to clearly describe the invention. In the drawings:

FIG. 9 depicts exemplary light source patterns for an exemplary embodiment of the invention which comprises light source groups having a blue light source, a red light source, and a near infrared light source.

FIG. 10 depicts exemplary vibrator patterns for an exemplary embodiment of the invention having a vaginal finger vibrator and a clitoral finger vibrator.

FIG. 11 depicts a table of preferred modes of vibration and light stimulation for a preferred embodiment of the improved stimulation sexual device of the invention.

DETAILED DESCRIPTION OF THE INVENTION

Figure 1:
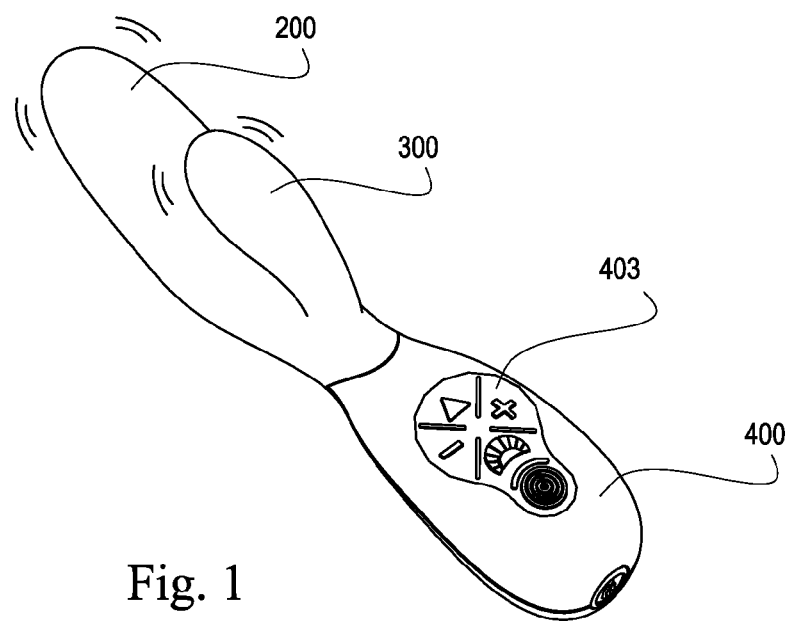
FIG. 1 depicts a perspective view of a preferred embodiment of the improved sexual stimulation device of the invention.

The following documentation provides a detailed description of the invention.

The invention is a device primarily intended for sexual stimulation of a female user. The improved sexual stimulation device of the invention may comprise a vaginal finger which may further comprise at least one therapeutic light source and a means for mechanical stimulation, which may comprise a vibrator; a clitoral finger which may further comprise at least one therapeutic light source and a means for mechanical stimulation, which may comprise a vibrator, and a handle which may comprise a keypad, controller, and a battery. The apparatus of the invention may use mechanical stimulation which may also be combined with a therapeutic light source or multiple therapeutic light sources so that, when applied to the body of a user it provides a therapeutic effect on the tissue of the vagina, and or vulva and or clitoris as described below. As used herein, "mechanical stimulation" shall mean any energy that exerts a perceivable movement to the tissue upon which it is applied.

The light source or light sources may be automatically powered when the mechanical energy element of the device is powered to an ON state, or may be configured so as to operate independently from the source or sources of mechanical energy. At least one light source, but preferably a plurality of light sources, provide light energy that exits the device at one or more points, preferably at a point along the length of the vaginal finger and also at a point along the length of the clitoral finger, which may irradiate the tissue in the vagina and may irradiate the body of the user on or near the clitoris or vulva. A preferred embodiment of the improved sexual stimulation device of the invention may comprise both a vaginal vibrator and a clitoral vibrator. The vaginal vibrator and clitoral vibrator may comprise any vibrating element small enough to fit within the envelope of vaginal and clitoral fingers of the invention. In a preferred embodiment, the vaginal vibrator and clitoral vibrator may be defined as a DC motor with offset weights mounted on the motor shaft such that the center of mass of the weight is offset from the axis of rotation of the motor. When such motors are powered to an on state, a vibration results from the offset nature of the center of mass of the weight mounted onto the vibrator motor shaft. While the vibrators of the preferred embodiment may exhibit any rate of vibration, a preferred range of vibration rate is 5,000 to 25,000 rpm. Such offset vibration motors are well known in the art for use as sources of vibration. One such vibration motor is supplied by Shenzhen Kinmore Motor Co. of Guangdong, China, part number FF-N20VA-09170 R6×4.8. However, any small source of vibration or mechanical energy may be used as the vibration elements of the invention. For instance, sonic pulses have been shown to have a vibratory effect, and may be used as a vibration source in either the vaginal finger, the clitoral finger, or both. An alternate embodiment of the invention may thus use at least one sonic pulse generator as a source of vibration; or, alternatively, may comprise vibration means that produce other forms of mechanical stimulation such as, for example, rubbing, tapping, pressure, and pressure that varies with time.

The invention may emit therapeutic light energy that irradiates the areas on or near the Grafenberg Spot inside the vagina, and may also irradiate the area on or near the clitoris and or elsewhere on the vulva or perineum. The Grafenberg Spot, often called the G-Spot, is defined as a bean-shaped area of the vagina. Some women report that it is an erogenous zone which, when stimulated, can lead to strong sexual arousal, powerful orgasms and female ejaculation. The G-Spot is typically described as being located one to three inches (2.5 to 7.6 cm) along the front (anterior) vaginal wall between the vaginal opening and the urethra and is a sensitive area. It is one objective of the invention to irradiate the G-spot and the area in proximity to the G-spot with light energy. However, the emitted light energy may also be directed through a broader or de-focused beam to surrounding tissues of the vagina. The concentration or de-focusing of light energy on specific areas such as the Grafenberg Spot or clitoris may be achieved by varying the placement of the light energy exit points of the invention, which may be a single or a plurality of exit points, and which may be covered by a wavelength transparent material, at appropriate positions on the apparatus in order for the exiting light energy to impact the intended area or areas. Similar alterations in light projection may be created by placing a lens or lenses over the light source or sources.

The light energy delivered by the device may be within a plurality of different ranges of wavelength. The light sources of the invention may be any light source such as Light Emitting Diode (LED), laser diode, organic LED (OLED) or any other light source which is compact enough to be enclosed in the apparatus. The wavelength of the light source, or sources, of the invention may be any wavelength, but is preferably in the range from 400 nm to 1000 nm. A plurality of light sources, which may be of different wavelengths, may be utilized; it is not necessary that a single source be used or that each of a plurality of sources emit light of the same wavelength. A preferred embodiment utilizes a plurality of light sources that, taken together, enables the invention to emit more than one wavelength range of light energy. The light energy used may be such to limit therapeutic penetration to less than 5 mm from the tissue surface and to have greater than 50% drop off of energy beyond such depth because the intended nerves and vessels that are the subject of stimulation are essentially superficial. Light energy may be delivered in continuous or pulsed form, where the pulses may take any shape and be of any duration. The power level of the light energy emitted by the light sources of the invention may be modulated in any fashion such as, for example, pulse width modulation, but preferably is controlled by increasing or decreasing the electrical current through the light source. "Light source" as used herein means a device that converts electrical energy to light energy such as an LED, OLED semiconductor laser, or any other device that exhibits this characteristic.

More specifically, a preferred embodiment of the improved sexual stimulation device of the invention comprises more specific ranges of bandwidth and output power of the light sources which are now described. The selection of bandwidth and output power of the therapeutic light sources for this preferred embodiment is based upon the demonstrated effects of photostimulation or photobiomodulation. It has been demonstrated that light sources emitting energy in the infrared and near infrared spectrum may provide photostimulation and photobiomodulation for the temporary relief of minor muscle and joint pain, muscle spasm, pain and stiffness, by promoting relaxation of the muscle tissue and temporarily increasing local blood circulation. As used herein, the term "light therapy" refers to the use of one or more light sources of any type that emits light with a wavelength between about 400 and 1000 nm.

Light therapy induces a variety of photo-thermal and photo-chemical processes in the body. Infrared light, near infrared light, and red light affect cellular mitochondria and activate surrounding enzymes resulting in the release of Nitric Oxide, ATP, and trigger photo neurological responses which result in changes in local pressure, temperature and permeability of cellular membranes, and stimulation of the immune, lymphatic and vascular systems. Organic nitrates are used every day in emergency rooms around the world to improve blood flow to the heart. There is also an inverse relationship between nitric oxide pathways and atherosclerosis. Patients with impaired NO pathways seem to have higher amounts of blood vessel plaques (narrowed blood vessels with poor blood flow and oxygen delivery to tissues). Over time, improved NO pathways may decrease atherosclerosis and create healthier "younger" blood vessels. Within the 400 to 1000 nm range is therapeutic blue light. Blue light energy has a bactericidal and bacteriostatic effect and has been shown to kill and disrupt growth of pathogenic bacteria. This inactivation mechanism, known to be oxygen dependent, is thought to be a result of the photoexcitation of naturally occurring endogenous porphyrins, which act as endogenous photosensitizers within the bacterial cells. This porphyrin excitation leads to energy transfer and, ultimately, the production of highly cytotoxic, oxygen-derived species, most notably, singlet oxygen. Although ultraviolet light is also lethal to many pathogenic bacteria, as we know, UV light is very detrimental to the skin. Blue light is much safer. Over time, blue light can safely lead to a reduction in pathogenic bacteria on skin and mucous membrane surfaces. Near IR light, also within this preferred spectrum of therapeutic light, damages the genetic material inside of fungus (DNA). DNA damage leads to impaired fungal growth. Over time the yeast population on skin and mucous membranes decreases. The use of IR light to treat toe nail fungus is now common medical practice.

Wavelength and power density are the two most prominent factors that determine the effectiveness of a light therapy source. The wavelength of the light source determines the absorption rate and penetration depth of the light energy in biological tissue. The power density of the light source, in combination with its wavelength, determines the effect the emitted light produces on body tissue, bacteria, and fungi. The effects of light therapy with therapeutic light have been studied for applications in, for example, pain relief and tissue healing: in, fact, about 2,700 clinical reports have been published in peer reviewed technical journals or conference proceedings with more than 70% of the reports indicating that light therapy is effective for tissue healing and pain relief. Clinical reports demonstrate that light therapy is effective, for instance, for the relief of muscle and joint pain, muscle spasm, pain and stiffness associated with arthritis, by promoting relaxation of the muscle tissue and temporarily increasing local blood circulation, without side effects. An even greater amount of data exist for the effects of light on bacteria and fungi.

It has also been shown that various pulse formats have a positive effect on photostimulation. Off-times between light pulses of 50 ms to 500 ms may have the greatest effect on cell organelles and plasma membranes. It is postulated that when this range of pulse formats is used, the re-oxidation of cytochrome c oxidase is optimized. This optimization leads to increase energy in the cell leading to improved blood flow and tissue repair. Pulsing of the light source is used to optimize the photobiological response though a temporal optimization as well as dosage control. Optimal dosages of light range from of 0.001 J/cm$^2$ up to 3000 J/cm$^2$. These dosages can be controlled through changing the intensity of the light source, changing the irradiation time, and by light source pulse shape and timing. Therapeutic results can be seen using intensities ranging from 0.001 W/cm$^2$ to 100 W/cm$^2$.

Studies have concluded that photostimulation can increase blood flow. Increased blood flow is critical for bodily functions and is an important factor in the excitement phase of sexual stimulation. Photostimulation enhances vasodilatation and proliferation of the microvasculature as well as increases the level of oxygen content to tissue of the irradiated area, in this case, the G-spot area, and the area surrounding the clitoris. In a recent study which compared a photostimulated group of human test subjects to a non-photostimulated group of human test subjects, the photostimulated group increased blood flow to the exposed area for over 12 hours. This study showed the capillaries of the human subjects were enlarged and thus blood flow increased as a result of photostimulation. Photostimulation activates the powerhouse for the cell to increase the rate at which it produces energy. This activation increases the production of critical biochemical substances such Nitric Oxide (NO) and Vascular Endothelial Growth Factors (VEGF). These growth factors also promote new blood vessel growth. These biological responses to light therapy explain why photostimulation can have both an immediate and cumulative effect on a subject's level of sensation during sexual stimulation. As noted above, it has also been shown in laboratory studies that light energy in certain bandwidths may also have an anti-bacterial effect. Clinical studies have verified this antibacterial effect on patients for light sources between 405 nm and 420 nm. It has also been shown that a combination of blue and red output from LEDs can be a very effective treatment of both inflammation and antibacterial results. Recent studies have shown that blue LEDs irradiating the skin may result in a seven to fifteen times increase in the NO level in tissue as deep as 18 mm below the skin's surface.

Based on the effects of light therapy on human tissue, it is a feature of a preferred embodiment of the invention that blue light sources emitting light energy in the ranges of 400 nm to 515 nm or 530 nm to 670 nm at a output of at least 300 millicandelas peak with a half-power output angle of +/−60 degrees, red light energy in the ranges of 610 nm to 640 nm at a output of 300 millicandelas peak with a half-power output angle of +/−60 degrees, and infrared light energy in the range of 820 nm to 880 nm at an output radiant flux of at least 300 mW peak with a half-power output angle of +/−60 degrees with each light source irradiating in pulses of equal on and off times between 50 msec and 500 msec, is one embodiment of many that creates the desired effects on tissues associated with the use of adult pleasure objects. Said effects are including, but not limited to, improved blood flow, improved blood vessel health, tissue regeneration, tissue tightening, improved cellular respiration, improved lubrication, decreased bacteria, decreased fungi, enhanced arousal and even pain relief. These effects may be directly caused in a user by use of the improved sexual stimulation device of the invention, as described herein. It is to be noted that this is just one of many embodiments of the invention, and any number of light sources emitting light energy within the range of 400 nm to 1000 nm at any radiant flux or millicandela output and angle may be used in any light source group of the invention. In order to emit the various bandwidths of light energy, each light source group may comprise more than one type of light source. For example, in the preferred embodiment described for which multiple frequencies of light are emitted by a light source group, a light source group may comprise light emitters which are defined as a plurality of LEDs, a plurality of lasers, or a plurality of light sources comprising a combination of LEDs and lasers. The light sources of the invention may be adapted to provide continuous output or provide output energy in pulses of any wave shape. "Half power angle" as used herein means the off-axis angle where the light source's luminous intensity is half the intensity at direct on-axis view. The axis of the light source is defined as the line of the vector of maximum intensity emanating from the light source.

In the various embodiments, the light energy may be pulsed on and off and may be any output energy with the ranges of output energies set forth herein. These light source output wavelengths may be administered in pulses that are in phase or out of phase as between light sources, and may be of any timing desired. It is an aspect of the invention that such light source pulse shape and timing may be, for some embodiments, programmable by use of a controller in communication with the light sources. The controller may be programmed by the user to produce a desired pulse shape and timing for the light sources of the invention. Alternatively the controller may be preprogrammed by a non-user.

In another preferred embodiment, these wavelengths, pulse widths, rest periods, and output power may be combined with mechanical energy such as that provided by an unbalanced vibration motor typical to that found in an adult sex toy, or any other method of mechanical energy delivery known in the art. In this manner, light therapy and mechanical stimulation, and, more specifically, vibration, may be applied together, or in alternating patterns of the user's choice, in order to achieve a desired stimulation effect.

In a preferred embodiment of the device, the light sources may be delivered to the tissue through an optical diffusing element, such as, for example, a silicone cover, to assure a homogeneous exposure of light to the selected tissue. In an alternate embodiment the device, the light sources may produce a selected pattern of optical energy to deliver optical energy to specific spots to provide differential exposure to unique spots on the tissue.

Yet further alternate embodiments will have preprogrammed light energy pulse patterns and or vibration patterns. The preferred embodiment comprises separate buttons for activating and choosing vibrations patterns and or light energy patterns.

In some of the specific preferred embodiments described herein, the mechanical stimulation example given is described as mechanical vibration produced by, for example and not by way of limitation, an offset vibrator motor. However, it is to be understood that the scope of the alternate embodiments of the invention includes all types of mechanical simulation devices and methods known in the art and which are adaptable to the invention without undue experimentation, such as sonic vibrators and mechanical manipulators of any type that produce rubbing, tapping, pressure, pressure that varies in intensity over time, and all other methods for mechanical stimulation.

Referring now to FIG. 1, a preferred embodiment of the sexual stimulation invention is shown in perspective view. The invention comprises vaginal finger 200, clitoral finger 300, handle 400 and keypad 403. The device is intended to be used primarily by a female user, who, in the most general case, would hold the invention with one hand or both hands by handle 400 and slidingly engage vaginal finger 200 in a vagina such that vaginal finger 200 applies vibration and vaginal light energy 201 within the vagina at or near the G-spot, while clitoral finger 300 may apply clitoral light energy 301 and vibration at or near a clitoris. The application of light energy and vibration at or near the G spot and clitoris in continuous fashion, or in patterns of vibration and light therapy as may be programmed into the invention, operate to cause more rapid and intense stimulation than is possible without the invention. One exemplary method of the invention may comprise the following steps: applying lubrication, a lubricating light coupling agent or a combination of such agents as desired to vaginal finger 200 or clitoral finger 300, or both, slidingly engaging vaginal finger 200 in a vagina while resting clitoral finger 300 on or near a clitoris, turning the vaginal light source group 202 and clitoral light source group 302 of the apparatus ON, turning the vaginal vibrator 204 and clitoral vibrator 304 of the apparatus ON, and holding and applying movement as desired by grasping handle 400. Alternatively, light source groups and or vibrators may be turned on prior to contact of fingers to body tissue. The invention may further comprise control circuitry located in the handle 400 of the invention which may be used to operate the invention in one or more of many possible operational modes which are discussed further herein. Keypad 403 may cover the internal circuitry of the invention in such a manner as to provide environmental protection for the circuitry while at the same time allowing a user to control the operation of the invention by pressing on keypad 403 which is in physical contact with and engages switches 500 in electrical communication with the control circuitry. In normal use, handle 400 remains outside the body of the user. It can further be seen from FIG. 1 that vaginal finger 200, clitoral finger 300 and handle 400 form a unitary structure. In an alternate embodiment, clitoral finger 300 may not be present: in this alternate embodiment vaginal finger 200 and handle 400 form a unitary structure.

Figure 2:
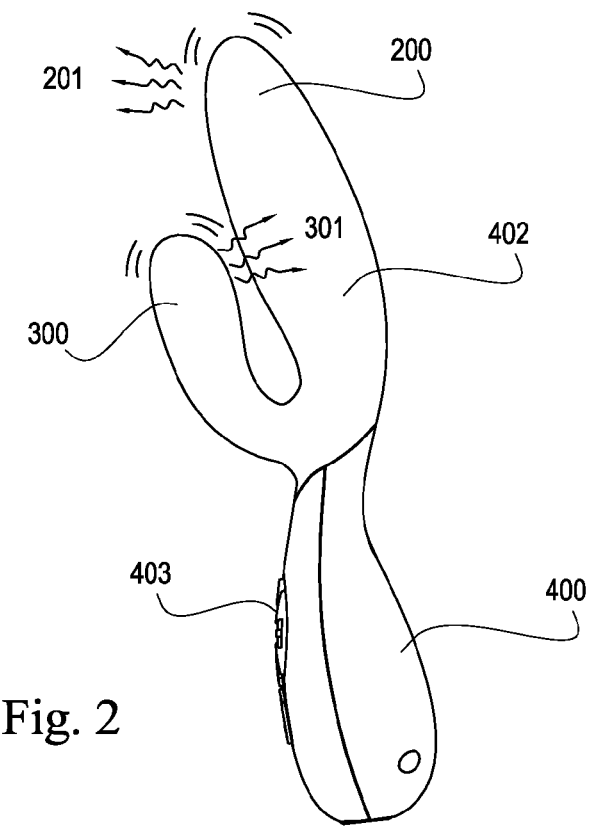
FIG. 2 depicts a side view of a preferred embodiment of the improved sexual stimulation device of the invention.

Referring to FIG. 2, vaginal finger 200 and the clitoral finger 300 are shown as vibrating, as during normal use in the preferred embodiment shown. Vaginal light energy 201 may irradiate body tissue at or near the G-pot as it radiates from a side of distal end of vaginal finger 200 through flexible cover 402. Clitoral light energy 301 may irradiate body tissue at or near the clitoris as it radiates from the distal end of clitoral finger 300 through flexible cover 402. Flexible cover 402 may cover vaginal finger 200 and clitoral finger 300 and may, in a preferred embodiment, provide a hypo allergenic cleanable covering for vaginal finger 200 and clitoral finger 300. Flexible cover 402 may be fabricated from any material suitable for this purpose and transmissive at frequencies of 400 nm to 1000 nm including, but not limited to, silicone. The use of silicone in this preferred embodiment exhibits reduced friction characteristics which facilitates sliding engagement of vaginal finger 200 into the vagina of a user and also facilitates reduced frictional properties when clitoral finger 300 is in contact with the body of a user on or near the clitoris. Keypad 403 covers switches 500 (not shown in FIG. 2) which, in this preferred embodiment, are located within handle 400. The anterior side of keypad 403 is directly pressed by a user, for example by a user's finger, in order to activate controls of the invention. The posterior side of keypad 403 comprises keyboard button nipples which engage switches 500 (not shown in FIG. 2) disposed on a surface of controller printed wiring board 418 (not shown in FIG. 2) when a user presses any of the depressible control buttons disposed on the anterior side of keypad 403. In this way, a user may control the improved sexual stimulation device 100 to power the device on or off, and to command to operate in any of the modes described herein.

Figure 3:
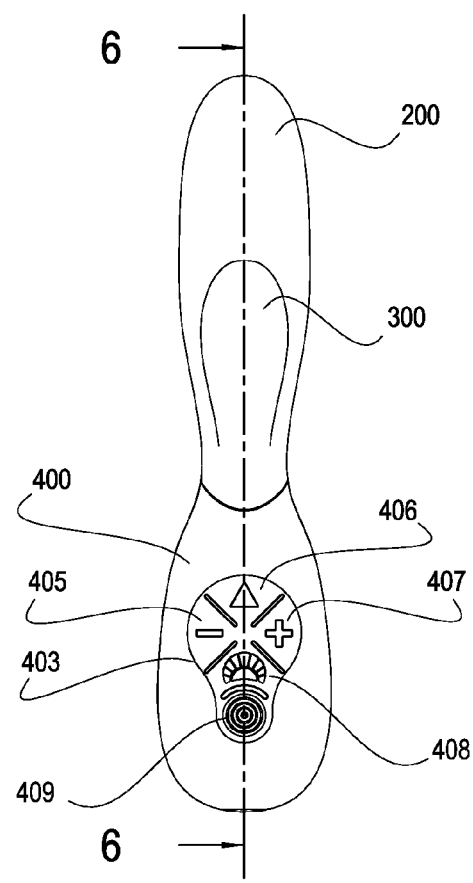
FIG. 3 depicts a front view of a preferred embodiment of the improved sexual stimulation device of the invention.

Referring now to FIG. 3, a front view of a preferred embodiment of the improved sexual stimulation device 100 of the invention is shown. Keypad 403 comprises a first depressible control button 405, a second depressible control button 406, a third depressible control button 407, fourth depressible control button 408, and fifth depressible control button 409 which are operated by a user to control the device. As described further herein, pressing downward on a depressible control button of the invention causes a keypad button nipple 428 (not shown in FIG. 3 but described further herein) disposed on the underside of keypad 403 to engage switches 500 (not shown in FIG. 3), which are in electrical communication with controller 501, providing commands as desired by the user to controller 501 (not shown in FIG. 3). The functions of the five depressible control buttons depicted in FIG. 3 are discussed hereinbelow. It is to be noted that the operational modes described herein are exemplary. Due to the programmable nature of controller 501 the depressible control buttons of the invention may be programmed to provide any combination of vibrator or light source on state, vibrator or light source off state, intensity of light, intensity of vibration, selection of pre-programmed vibration pulse shapes or continuous operation, selection of pre-programmed light energy pulse shapes or continuous operation, test modes, light energy and vibration display modes, and the like, may be programmed into the invention, selected and operated by a user pressing the depressible control buttons of the invention, which may be programmed to command any of these operations. Mechanical stimulating components other than vibrating motors may be substituted for vibrating motors and similarly controlled.

Figure 4:
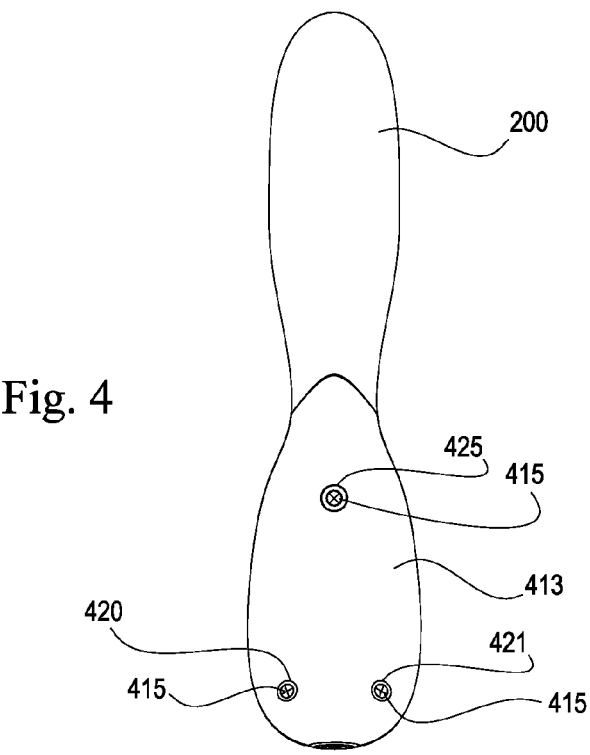
FIG. 4 depicts a rear view of a preferred embodiment of the improved sexual stimulation device of the invention.

Referring now to FIG. 4, a rear view of a preferred embodiment of the improved sexual stimulation device 100 of the invention is depicted. Shown in FIG. 4 are first cavity 420, second cavity 421 and third cavity 425, which may provide recessed insertion points for handle rear cover fastener 415 which are inserted through first cavity 420, second cavity 421 and third cavity 425 and are threadingly engaged into receiving female threads located on main support structure 412 (not shown in FIG. 4), and are therefore used to hold handle rear cover 413 into place. Alternatively, such cavities may be replaced by molded pins communicating with glue bosses rather than screw bosses.

Figure 5:
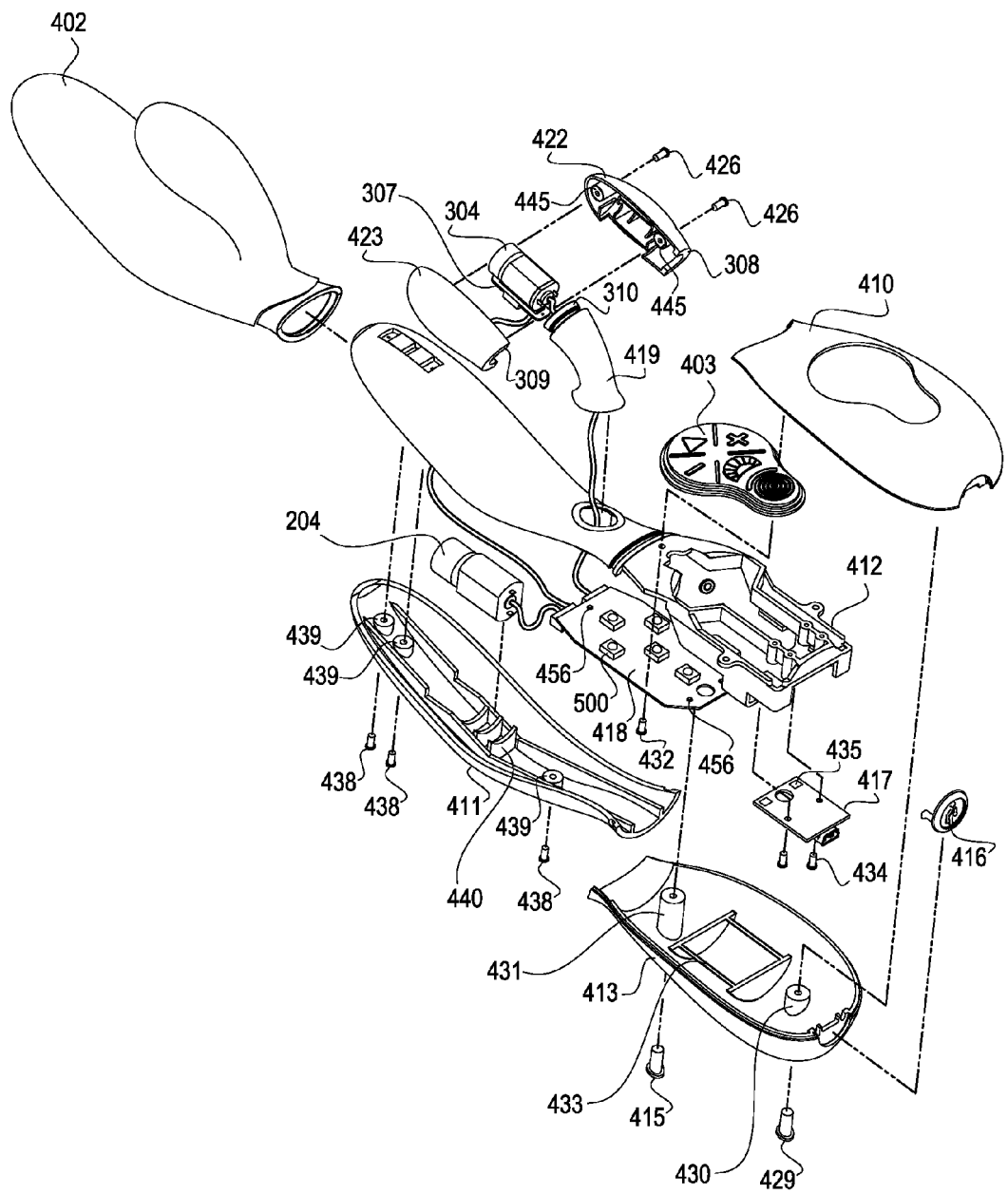
FIG. 5 depicts an exploded view of a preferred embodiment of the improved sexual stimulation device of the invention.

Referring now to FIG. 5, an exploded view of the preferred embodiment of the improved sexual stimulation device 100 of the invention is depicted. It is to be noted that, while a specific structure is shown in FIG. 5, there are many equivalent structures which are covered by the claims, and that the scope of the invention includes equivalent structures as would be understood by a person of ordinary skill in the mechanical arts.

Still referring to FIG. 5, main support structure 412 is an elongate mechanical structure, preferably molded from plastic, but also, if desired, cast from metal or machined from any stable substantially rigid material such as plastic, phenolic, or other materials known in the art. Main support structure 412 provides support and attachment points for the various components and internal elements of the invention. The attachment points may generally be female bosses which are adapted to receive male threaded fasteners, and which may be threaded with female threads or may receive self-threading male threaded fasteners. All such female bosses may also serve as adhesive bosses to receive male pins and adhesive. Bosses, screw and pins may be decreased in number or removed in entirety if ultrasonic or similar welding is used to secure surfaces.

Still referring to FIG. 5, the attachments of keypad 403 and handle front cover plate 410 are discussed. Keypad 403 rests upon main support structure 412 and may be preferably bonded into place thereon using any suitable adhesive for bonding keypad 403, which may be fabricated from, for example, silicone, silicone compounds or any flexible polymer material. Alternatively, keypad 403 may be allowed to simply rest in place, sandwiched between handle front cover plate and main support structure 412. Keypad 403 may comprise a plurality of keypad button nipples 428 (not shown in FIG. 5) that act to engage switches 500 when a depressible control button is depressed. Handle front cover plate 410 may be attached to main support structure 412 by handle front cover fastener 429, which may reside in handle front cover fastener recess 430, with the male threaded portion of handle front cover fastener 429 protruding thru handle front cover fastener recess 430 and being threadingly received by a female boss disposed on the underside of handle front cover 410 (not shown in FIG. 5). Likewise, handle front cover plate 410 is attached at its forward end by second handle front cover fastener 432 which may pass through an opening in main support structure 412 to be threadingly received by a female boss disposed on the underside of handle front cover 410 (not shown in FIG. 5). In this manner, keypad 403 and handle front cover plate 410 are held in place, allowing keypad button nipples 428 (not shown in FIG. 5) to rest, or nearly rest, upon switches 500 such that depression of any of the depressible control buttons 405-409 cause activation of a switch underneath, sending commands to controller 501 (not shown in FIG. 5) on controller printed wiring board 418.

Referring still to FIG. 5, the attachment of controller printed wiring board 418, USB port printed wiring board 417, handle rear cover 413, and battery 503 (not shown in FIG. 5) is discussed. USB port printed wiring board 417 may be structurally attached to main support structure 412 by USB printed wiring board fasteners 434, which pass through clearance holes in USB port printed wiring board 417 to be threadingly received by female bosses disposed on the underside of main support structure 412 (not shown in FIG. 5). USB printed wiring board fasteners 434 may be electrically connected to controller printed wiring board 418 by wires or direct solder connection between them at USB printed wiring board solder attachments 435 or equivalent electrical connection structures known in the art. Alternatively, USB port printed wiring board 417 may be fabricated as a unitary element of controller printed wiring board 418. USB port printed wiring board 417 may comprise an electrical Universal Serial Bus (USB) charging port connector 451 to a charging or programming mating connector; however, the form of the electrical connection may take any form known or conceived in the electrical arts such as USB, micro-USB, custom design connection, or any other standard electrical connection suitable to fit within the envelope allowable. Controller printed wiring board 418 attaches to main support structure 412 by threaded fasteners (not shown in FIG. 5) passing through clearance holes 456 to be threadingly received by female bosses disposed on the underside of main support structure 412 (not shown in FIG. 5). Rear handle cover 413 is attached to main support structure 412 by handle rear cover fastener 415, which resides in handle rear cover fastener recess 431 with the male threaded portion of handle rear cover fastener 415 protruding through handle rear cover fastener recess 431 and being threadingly received by a female boss disposed on the underside of main support structure 412 (not shown in FIG. 5). Battery 503 (not shown in FIG. 5 for clarity sake, but shown in FIG. 6) may be sandwiched in place between the underside of controller printed wiring board 418 and battery support structure 433, and may be electrically connected with battery wires 436 (not shown in FIG. 5, but shown in FIG. 6) to controller printed wiring board 418 by a solder or other standard technique for making electrically conductive connection. Battery 503 may further comprise a battery compressive covering 437 such as compressible foam (not shown in FIG. 5 but shown in FIG. 6), or layers of compressive material fabricated from any suitable compressive material, so that it is sandwiched and held in place between the underside of controller printed wiring board 418 and battery support structure 433 with a compressive fit to prevent movement of the battery during shipping and use. Charging port connector 451 may be wired to communicate directly with controller 501 to facilitate programming. Likewise, a Bluetooth® chip and or WiFi chip may be used for similar purpose. Alternative methods of charging well known in the art such as inductive charging may be substituted for USB charging. The invention may further comprise an inductive charging circuit as is known in the art, such that the device may be charged by simply placing it in an inductive charging cradle.

Still referring to FIG. 5, vaginal finger rear cover plate 411 may attach to main support structure 412 by vaginal finger rear cover fasteners 438 which reside in vaginal finger rear cover recesses 439 with the male threaded portion of handle rear cover fastener 438 protruding through vaginal finger rear cover recesses 439 and being threadingly received by female bosses disposed on the underside of main support structure 412 (not shown in FIG. 5). Vaginal vibrator 204 may be supported on its underneath side by vaginal finger vibrator retaining structure 440 when vaginal finger rear cover plate 411 is attached in place. Vaginal vibrator 204 is further held in place by main support structure vaginal supports 441 (not shown in FIG. 5 but shown in FIG. 6). Vaginal vibrator 204 may be engaged with main support structure vaginal vibrator supports 441 with a press fit engagement and for further retention may be bonded into place with adhesives.

Figure 8:
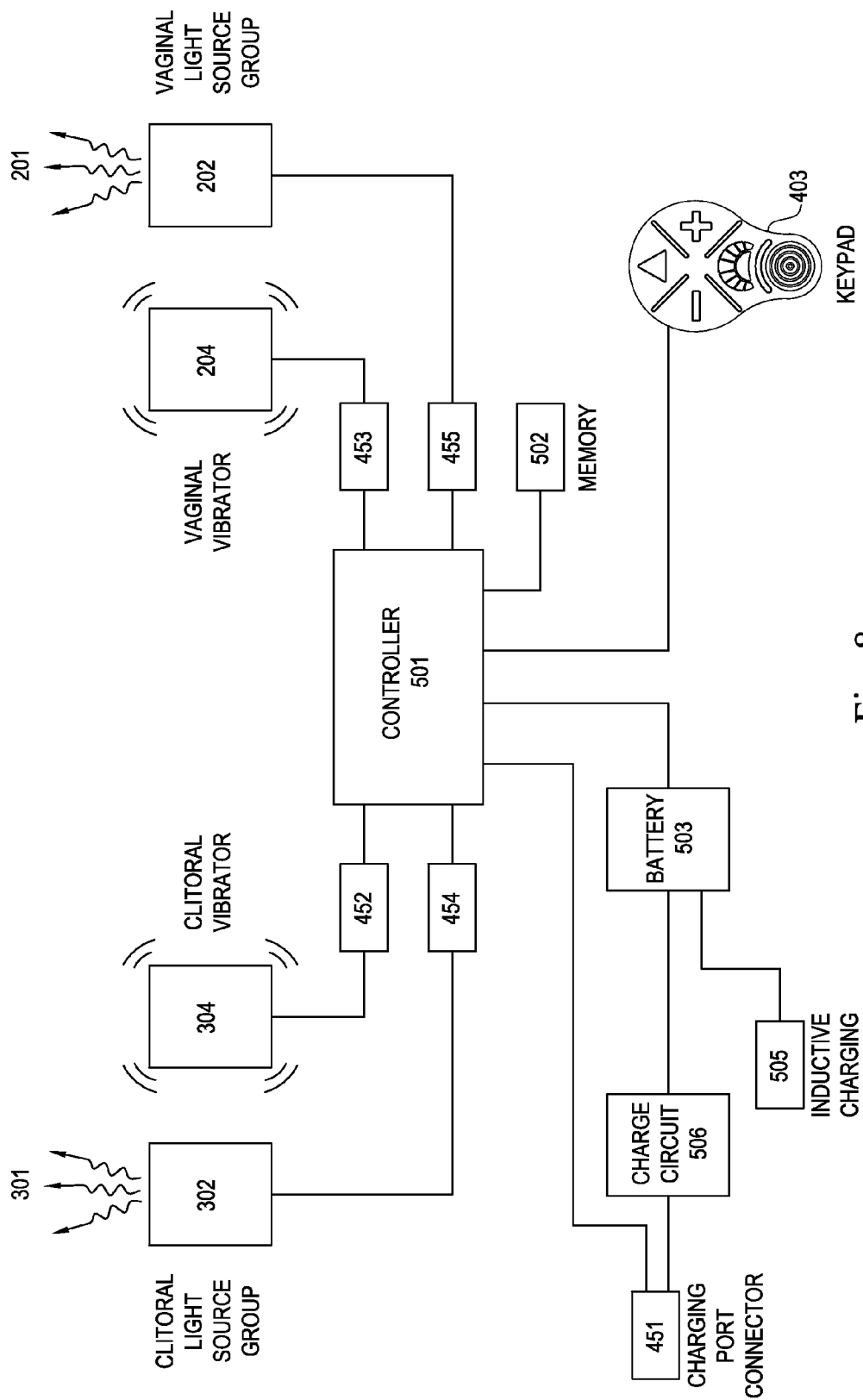
FIG. 8 depicts a functional block diagram of a preferred embodiment of the improved sexual stimulation device of the invention.

Still referring to FIG. 5, clitoral finger base 419 rests upon main support structure 412 and is held in place by operation of flexible cover 402 which may provide, preferably, a covering with a slight compressive fit over clitoral finger 300 as well as vaginal finger 200. Clitoral finger base 419 is preferably fabricated from a flexible material such as, for instance, silicone or any similar flexible material. A preferred embodiment of the invention further comprises a clitoral finger first cover 422 and a clitoral finger second cover 423 of similar opposed cross section such that, when brought together as shown in FIG. 5 create a substantially smooth shape. While a preferred shape for the assembled clitoral finger is depicted in FIG. 8, the shape of clitoral finger 300 may be any shape suitable for pleasant contact on or near the clitoris of the user. Clitoral vibrator 304 may be attached to clitoral finger printed wiring board 307(not shown in FIG. 5), upon which clitoral light source group 302 (not called out in FIG. 5) may also be mounted with electrical connection thereto. Clitoral finger printed wiring board 307 is held in place in clitoral finger vibrator structure 457 by clitoral finger printed wiring board retaining structure 444 (not shown in FIG. 5, but shown in FIG. 6) formed in clitoral finger first cover 422 which substantially forms a groove adapted to accept clitoral printed wiring board 307 in a press fit engagement. Clitoral vibrator 304 may be attached to clitoral finger printed wiring board 307 by adhesive bonding or any other means of attachment known in the mechanical arts. Clitoral finger first cover 422 is attached to clitoral finger second cover 423 by clitoral finger fasteners 426 which reside in clitoral finger first cover fastener recesses 445 with the male threaded portion of clitoral finger fasteners 426 protruding through clitoral finger first cover fastener recesses 445 and being threadingly received by female bosses disposed on an inside surface of clitoral finger second cover 423 (not shown in FIG. 5). Clitoral finger base 419 may further comprise clitoral finger base retaining groove 310 which is adapted to receive clitoral finger first cover retaining ring half 308 and clitoral finger second cover retaining ring half 309 such that, when clitoral finger fasteners 426 are installed and tightened, clitoral finger first cover retaining ring half 308 and clitoral finger second cover retaining ring half 309 are brought together to lock the assembled clitoral finger 300 components into place by operation of the retention properties of clitoral finger base retaining groove 310 holding clitoral finger first cover retaining ring half 308 and clitoral finger second cover retaining ring half 309 in place, as is shown in cross section view in FIG. 6.

Still referring to FIG. 5, main support structure 412, handle front cover plate 410, handle rear cover 413, vaginal finger rear cover plate 411, clitoral finger first cover 422, and clitoral finger second cover 423 may be fabricated from any material rigid enough to structurally support the assembly and repeated use of the improved sexual stimulation device 100 of the invention. Preferably, these components may be fabricated from any plastic material in order to facilitate ease of manufacture and minimize weight. Still within the scope of the invention, but less preferred, are other rigid materials such as metals, phenolic materials, organic materials, or any other materials rigid enough to support the assembly and repeated use of the invention. Such materials are known in the art.

Figure 6:
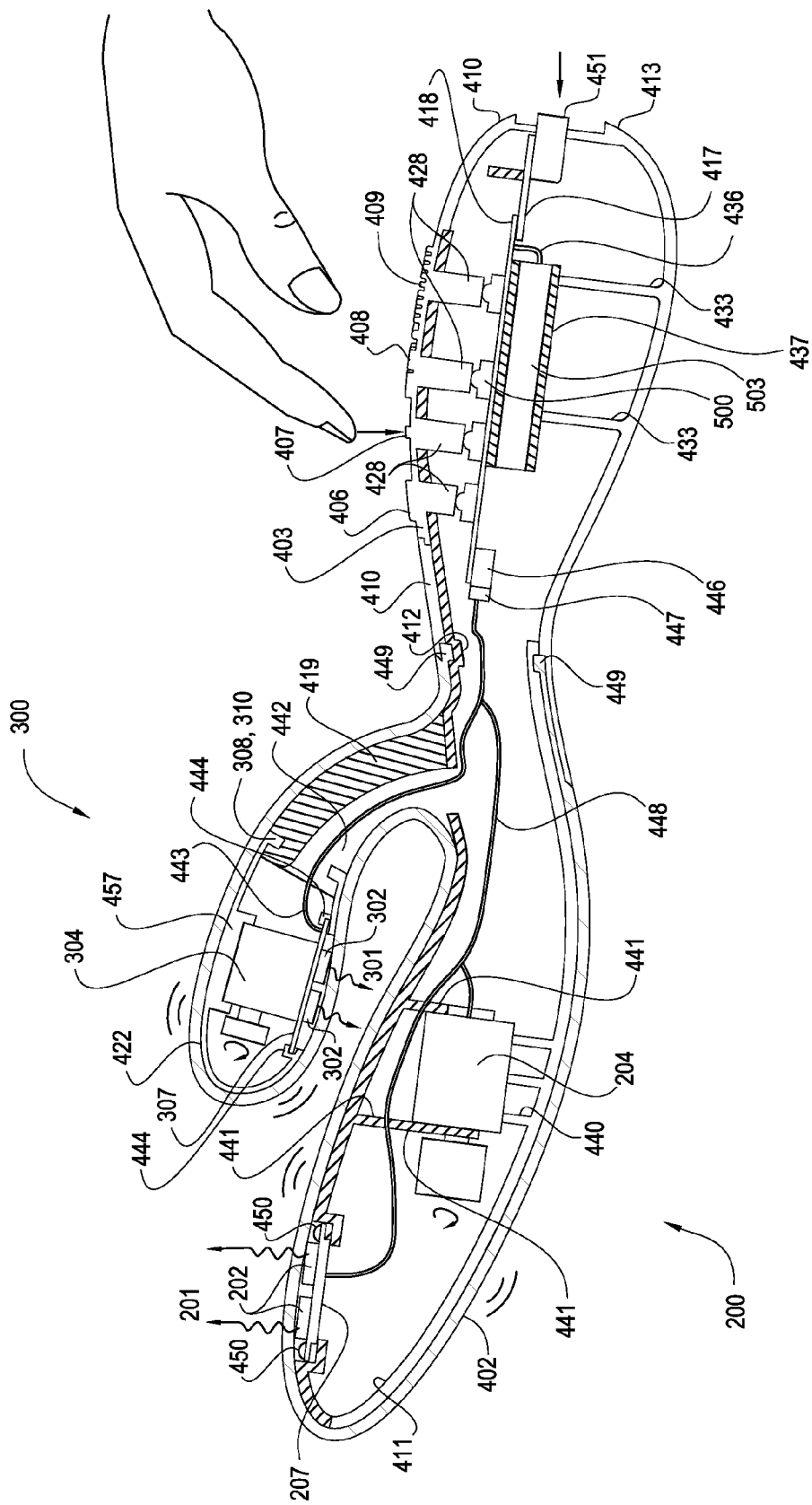
FIG. 6 depicts a cross-sectional view of a preferred embodiment of the improved sexual stimulation device of the invention, further depicting the location of the electrical components of the invention.

Referring now to FIG. 6, a cross sectional view of a preferred embodiment of the improved sexual stimulation device 100 of the invention is depicted. Keypad 403 is shown as being pressed by the finger of a user by depressing, for example, third depressible control button 407 which causes a keypad button nipple 428 to depress and activate the corresponding switch 500, which is mounted on controller printed wiring board 418. Thus a user may command and operate the improved sexual stimulation device 100 of the invention as desired by turning it on or off, manually changing modes, and commanding pre-programmed modes of operation, or the like. Battery 503 may be sandwiched in place between the underside of controller printed wiring board 418 and battery support structure 433, and may be electrically connected with battery wires 436 to controller printed wiring board 418 by a solder or other standard technique for making electrically conductive connection. Battery 503 may further comprise a battery compressive covering 437, or layers of compressive material fabricated from any suitable compressive material, so that it is sandwiched and held in place between the underside of controller printed wiring board 418 and battery support structure 433 with a compressive fit to prevent movement of the battery during shipping and use. Controller printed wiring board connector 446 mates mechanically and electrically with wiring connector 447, enabling the connection and disconnection of clitoral finger wires 443 and vaginal finger wires 448 from controller printed wiring board 418 to facilitate assembly and repair.

Still referring to FIG. 6, flexible cover 402 covers vaginal finger 200 and clitoral finger 300 with a slight compressive fit, and may be further captured in place by flexible cover retaining step 449 which may be received by a matching groove in main support structure 412 and rear handle cover 413 as shown in FIG. 6. Further, Vaginal vibrator 204 may be supported on its underneath side by vaginal finger vibrator retaining structure 440 when vaginal finger rear cover plate 411 is attached in place to vaginal vibrator 204 is further held in place by main support structure vaginal supports 441. Vaginal vibrator 204 may be engaged with main support structure vaginal vibrator supports 441 with a press fit engagement and for further retention may be bonded into place with adhesives. Vaginal finger printed wiring board 207 is held in place by vaginal printed wiring board fasteners 450 which are received by holes in main support structure 412 and which are adapted to receive vaginal printed wiring board fasteners 450, which may be standard threaded fasteners, self-tapping or any other fastener type known in the art. When vaginal printed wiring board 207 is mounted as shown, vaginal light energy 201 from vaginal light energy source group 202 may exit vaginal finger 200 by passing through flexible cover 402 which is transmissive at light frequencies stated herein. Vaginal finger wires 448 establish electrical connection between vaginal printed wiring board 207, vaginal vibrator 204, and controller printed wiring board 418. Clitoral finger printed wiring board 307 is held in place in clitoral finger 300 by clitoral finger printed wiring board retaining structure 444 formed in clitoral finger first cover 422 which substantially forms a groove adapted to accept clitoral printed wiring board 307 in a press fit engagement. Clitoral vibrator 304 may be attached to clitoral printed wiring board 307 by adhesive bonding or any other means of attachment known in the mechanical arts. When clitoral printed wiring board 307 is mounted as shown, clitoral light energy 301 from clitoral light energy source group 302 may exit clitoral finger 300 by passing through flexible cover 402 which is transmissive at light frequencies stated herein. Clitoral finger wires 443 establish electrical connection between clitoral printed wiring board 307, clitoral vibrator 304, and controller printed wiring board 418. Clitoral finger base 419 rests upon main support structure 412. Clitoral finger wires 443 pass through clitoral finger base channel 442. Clitoral finger base 419 may further comprise clitoral finger base retaining groove 310 which is adapted to receive clitoral finger first cover retaining ring half 308 and clitoral finger second cover retaining ring half 309 such that, when clitoral finger fasteners 426 (not shown in FIG. 6) are installed and tightened, clitoral finger first cover retaining ring half 308 and clitoral finger second cover retaining ring half 309 (not shown in FIG. 6) are brought together to lock the assembled clitoral finger 300 components into place by operation of the retention properties of clitoral finger base retaining groove 310 holding the retainer ring halves, 308 and 309, in place.

Charging port connector 451 is electrically and mechanically attached to USB port printed wiring board 417, and protrudes through an opening formed in handle front cover plate 410 and handle rear cover 413 when they are assembled as described herein.

Figure 7A:
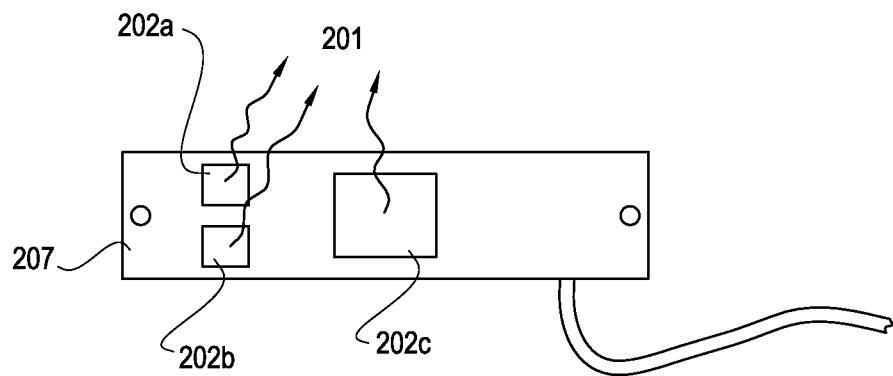
FIG. 7a depicts a top view of the vaginal printed wiring board of a preferred embodiment of the invention, depicting a clitoral source group in electrical and mechanical communication with a clitoral finger printed wiring board.
Figure 7B:
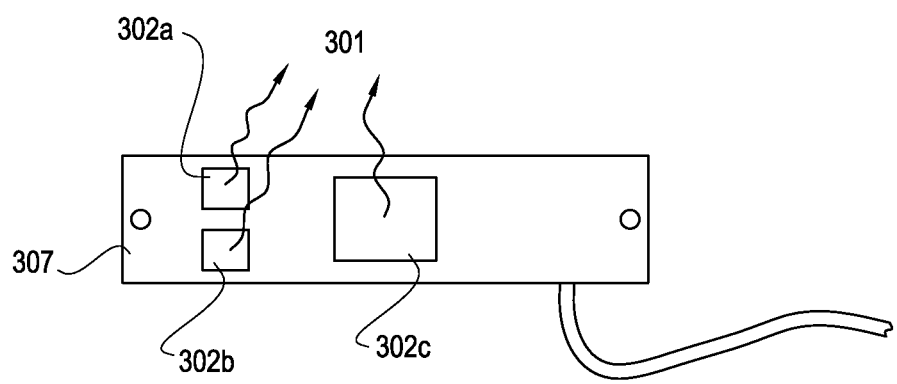
FIG. 7b depicts a top view of a clitoral printed wiring board of a preferred embodiment of the invention, depicting a vaginal source group in electrical and mechanical communication with a vaginal finger printed wiring board.

Referring now to FIG. 7a and FIG. 7b, details of a preferred embodiment of vaginal finger printed wiring board 207 and clitoral finger printed wiring board 307 are depicted. Both of these printed wiring boards may contain one or more light sources in electrical connection with wiring that is in electrical connection with controller printed wiring board 418 as follows. Referring first to FIG. 7a, vaginal finger printed wiring board 207 may comprise vaginal light source group 202 which is itself comprised of at least one light source, but preferably is comprised of a variety of light sources in order to combined a variety of frequencies of light that may be radiated as vaginal light energy 201. Vaginal light source group 202 may comprise any number of light sources. In the preferred embodiment shown in FIG. 7a, three vaginal light sources 202a, 202b and 202c are depicted as comprising vaginal light source group 202. Each light source may consist of one or more diodes. Vaginal light sources 202a, 202b and 202c may be soldered to vaginal finger printed wiring board 207 to provide electrical and mechanical connected thereto, or may be attached to vaginal finger printed wiring board 207 in any manner known in the electrical assembly arts. In an alternate embodiment, the light sources of vaginal light source group 202 may be individually attached to main support structure 412 or its equivalent and connected with discrete wires (not shown in FIG. 7a) to controller printed wiring board 418. Referring now to FIG. 7b, clitoral finger printed wiring board 307 may likewise comprise clitoral light source group 302 which is itself comprised of at least one light source, but preferably is comprised of a variety of light sources in order that a variety of frequencies of light may be radiated as clitoral light energy 301. Clitoral light source group 302 may comprise any number of light sources. In the preferred embodiment shown in FIG. 7b, three clitoral light sources 302a, 302b and 302c are depicted as comprising clitoral light source group 302. Each light source may consist of one or more diode. Clitoral light sources 302a, 302b and 302c may be soldered to clitoral finger printed wiring board 307 to provide electrical and mechanical connected thereto, or may be attached to clitoral finger printed wiring board 307 in any manner known in the electrical assembly arts. In an alternate embodiment, the light sources of clitoral light source group 302 may be individually attached to main support structure or its equivalent and connected with discrete wires (not shown in FIG. 7b) to controller printed wiring board 418. In a preferred embodiment, the light sources of vaginal light source group 202 may be defined as light source 202a and 202b, each having a "blue" LED emitting wavelengths between 400 nm to 515 nm and a "red" LED emitting wavelengths between 610 nm to 640 nm for a total of 4 LEDs; and light source 202c comprising an infrared LED emitting wavelengths between 820 nm to 880 nm. Likewise, in preferred embodiment, the light sources of clitoral light source group 302 may be defined as light as light source 302a and 302b, each having a "blue" LED emitting wavelengths between 400 nm to 515 nm and a "red" LED emitting wavelengths between 610 nm to 640 nm for a total of 4 LEDs and light source 302c comprising an infrared LED emitting wavelengths between 820 nm to 880 nm. While these exemplary light source groups are discussed herein as regards the modes of operation of the invention, it is to be understood that the exact number of light sources in each light source group is variable, as well as are the frequencies of light emitted, the output power of the emitted light energy, and the modes of operation. Thus, a light source group may consist of two "blue" LEDs, three infrared LEDs, only one "red" LED, and LEDs with differing wavelengths and output powers other than the blue, red and infrared light sources described above, and so on. All combinations of light source types are considered within the scope of the claimed invention. Furthermore, alternate embodiments of the invention may comprise a light source or light sources disposed only in clitoral finger 300 and not in vaginal finger 200, and vice versa. Additionally, alternate embodiments may utilize light sources known in the art that are disposed in the handle of the device or external to the device whereby therapeutic light energy is transmitted to vaginal and or clitoral finger through light tubes or fibers.

Referring now to FIG. 8, an electrical block diagram of the sexual stimulation device 100 of the invention is depicted. The invention is an electro-mechanical apparatus that may comprise a vaginal light source group 202, a clitoral light source group 302, a vaginal vibrator 204, a clitoral vibrator 304, a controller 501, a memory 502, a charging circuit 506, an inductive charging circuit 505, a charging and programming port connector, such as a USB connector, 451, and a keypad 403. Controller 501 may reside on controller printed wiring board 418 (not shown in FIG. 8) and be soldered thereto. Controller 501 may be a single electrical device or a plurality of electrical devices that allow control inputs to be accepted from a user through the use of keyboard 403, by a user depressing one or more depressible control buttons as hereinbefore described. Controller 501 may comprise any electrical components known in the art for accepting commands and providing an output based on user inputs, preprogrammed data, or combinations thereof. Thus, controller 501 may comprise programmable logic devices, non-field-programmable firmware devices, field programmable firmware devices, microprocessors, microcontrollers, discrete logic and other logic devices adapted to perform the functions of receiving an input from a user and commanding the vibrators or other motors and light sources of the invention to operate in any desired modes, which are further defined herein. Memory 502 may be integral with the controller 501, such as "on-board memory" or may be one or more separate memory devices in electrical communication with controller 501. Memory 502 may be utilized to store pre-programmed modes of operation and to store other information as may be required by controller 501. Battery 503 is in electrical communication with and provides power to drive controller 501, memory 502, clitoral light source group 302, clitoral vibrator 304, vaginal vibrator 204, vaginal light source group 202, and any other electrical devices of the invention. Battery 503 may drive these devices directly or may drive them through their electrical connection with controller 501. Battery 503 may also be in electrical communication with charge circuit 506, which may condition power received through charging port connector 451. Alternatively, charging port connector 451 may be in direct communication with battery 503 for directly charging the battery. Battery 503 may also be in electrical communication with inductive charging circuit 505, which may be adapted to produce a charging current when placed in proximity with magnetic field, as is known in the art of inductive charging circuits. In a further alternate embodiment, not shown in FIG. 8, battery 503 may comprise a replaceable battery or group of batteries, such that they are replaced with a new battery or group of batteries when a given discharge level is reached, for example, when battery 503 is no longer able to power the improved sexual stimulation device 100 of the invention to a user's satisfaction. In any of the embodiments described herein, battery 503 may be a single battery or a group of batteries. Also, the electrical connection at charging port connector 451 may be any connector suitable to fit within the envelope of the invention and provide electrical communication as described herein. Thus, any type of electrical connector, whether a standard connector or a custom connector, may be used and is therefore within the scope of the claims. In a still further embodiment, charging port connector 451 may be in electrical communication with controller 501 such that modes of operation, firmware for operation of the vibrators and light sources of the invention, programming of keypad button functions, and other programmable aspects of the invention may be download and or uploaded and used by controller 501 and stored in memory 502. Thus, charging port connector 451 may also be a programming port.

Still referring to FIG. 8, controller 501 may further comprise an infrared or RF wireless interface such as, for example, the interface known as Bluetooth®, the interface known as WiFi, the interface known as Near Field Communications (NFC) or any other wireless interface as is known by persons of ordinary skill in the art, in order to wirelessly control the invention and download new or changed modes of operation information and or other information and the like to be stored in either controller 501 or memory 502, or the like. Any type of information may be downloaded and stored in this manner. Such wireless interfaces are well known in the electronic arts and, as such, do not require undue experimentation to understand and implement.

Still referring to FIG. 8, controller 501 may be in electrical communication with a vaginal light source group 202 through vaginal finger wires 448 (not shown in FIG. 8), a clitoral light source group 302 through clitoral finger wires 443 (not shown in FIG. 8), a vaginal vibrator 204 through vaginal finger wires 448 (not shown in FIG. 8), and a clitoral vibrator 304 through clitoral finger wires 443. These devices may be powered off, powered on, pulsed, operated continuously, or driven to various levels of output power directly by the circuitry of controller 501, or by drivers 452, 453, 454, or 455 which may be in electrical communication with controller 501, as the user desires. These drivers may be discrete electric circuits or may be incorporated directly in controller 501 as "on-board" drivers. Vaginal light source group 202, clitoral light source group 302, vaginal vibrator 204, and clitoral vibrator 304 may thus be individually commanded by controller 501 to operate in any patterns desired by the user, which patterns may be coordinated in order to achieve a desired stimulation effect in the user. The patterns of control are discussed below.

Still referring to the preferred embodiment of the invention depicted in FIG. 8, controller 501, memory 502, charge circuit 506, and drivers 452, 453, 454, and 455 are located on controller printed wiring board 418 (not shown in FIG. 8), which may be located in handle 400 (not shown in FIG. 8) along with keypad 403. Battery 503, charging port connector 451 and inductive charging circuit 505 may also be located in the handle 400 (not shown in FIG. 8), and may be connected through discrete wires preferably with solder attachments. Vaginal vibrator 204 and vaginal light source group 202 may be located in vaginal finger 200 (not shown in FIG. 8) and clitoral vibrator 304 and clitoral light source group 302 may be located in clitoral finger 300 (not shown in FIG. 8). In alternate embodiments of the invention, the various components comprising the invention may be located in any location within the invention and interconnected electrically as is conceivable by the techniques and methods known by persons of ordinary skill in the electro-mechanical arts. Such alternate embodiments are within the scope of the claims, as are equivalent structures and components.

Exemplary modes of operation and control of the states and patterns used to operate the vibrators and light sources of the invention are now discussed. While a preferred embodiment is discussed for purpose of description herein, it is to be understood that the programmable nature of the invention allows any variation, and therefore any pattern, of intensity and wave shape for both the light sources and vibration of the invention. Thus, the embodiment shown is exemplary only. The intensity of vibration of clitoral vibrator 304 and vaginal vibrator 204 may be controlled by pulse width modulation (PWM) control of power to the vibrator motor by controller 501, such that, for example, a 50% duty cycle represents LOW power, a 75% duty cycle represents MEDIUM power, and a 100% duty cycle represents HIGH power. These designations of power level may be set as desired, such that various terms may be given to corresponding duty cycles, and any number of power levels, which are the result of variation of the pulse width of the PWM drive signal driving the vibrators, may be defined as desired. It is a feature of controller 501 that any of the vibrators of the invention may be driven at any duty cycle desired, whether constant or in a pattern such as a pulsed pattern, sinusoidal pattern, or otherwise, based upon the desire of the user as programmed into controller 501, and, preferably, stored into memory 502.

A user may depress the depressible buttons 405-409 on keypad 403 to control operation of the invention in the following manner. It is to be understood that, due to the programmable nature of the invention, any combination of vibration patterns and light patterns may be programmed into controller 501 and memory 502. The modes of operation described hereinbelow are exemplary and not limiting. In the exemplary embodiment used in for description of operating modes below, vaginal light source group 202 comprises "blue" LEDs, "red" LEDs and an infrared LED; and likewise clitoral light source group 302 comprises "blue" LEDs, "red" LEDs and an infrared LED. Again, these configurations of light source groups are merely exemplary. Furthermore, in the exemplary embodiment used in for description of operating modes below, vaginal finger 200 comprises a vaginal vibrator 204 and clitoral finger 300 comprises clitoral vibrator 304.

In the exemplary embodiment, the invention may be powered on by pressing first depressible control button 405 and third depressible control button 407 simultaneously for three seconds, which may power the invention ON in a base operating mode. In this mode, vaginal vibrator 204 operates in a continuous LOW power state; the blue, red and infrared LEDs of vaginal light source group 202 are powered in the base pattern depicted in FIG. 9; clitoral vibrator 304 operates in a LOW power state; and the blue, red and infrared LEDs of clitoral light source group 302 are also powered in the base pattern depicted in FIG. 9. Next, pressing and releasing second depressible control button 406 may cause controller 501 to command clitoral vibrator 304 and the light sources of clitoral light source group 302 to an OFF state. Next, pressing and releasing second depressible button 406 may cause controller 501 to command clitoral vibrator 304 to a continuous LOW power state, and cause the light sources of clitoral light source group 302 to operate in the base pattern state of FIG. 9, while commanding vaginal vibrator 204 and the light sources of vaginal light source group 202 to an OFF state. Next, pressing and releasing second depressible button 406 may cause controller 501 to command vaginal vibrator 204 and clitoral vibrator 304 to pulse between OFF and ON states in an out-of-phase pattern in LOW power mode, while commanding the light sources of both vaginal light source group 202 and clitoral light source group 302 to operate in the base pattern shown in FIG. 9. Next, pressing and releasing second depressible button 406 may cause controller 501 to command vaginal vibrator 204 and clitoral vibrator 304 to pulse between OFF and ON states in an in-phase pattern with a high pulse rate, such as, for example, greater than 2.0 Hz pulse rate, in LOW power mode, while light source groups 202 and 302 remain operating in the base pattern shown in FIG. 9. It is to be understood that the pulse rate may be any rate commanded by controller 501. Next, pressing and releasing second depressible button 406 may cause controller 501 to command vaginal vibrator 204 and clitoral vibrator 304 to operate in a substantially sinusoidal-shaped intensity profile, in which the PWM signal driving each vibrator is characterized by a pulse width that varies sinusoidally. Next, pressing and releasing second depressible button 406 may cause controller 501 to command vaginal vibrator 204 and clitoral vibrator 304, and light source groups 202 and 302, back into the base operating mode described above in which vaginal vibrator 204 operates in a continuous LOW power state; the blue, red and infrared LEDs of vaginal light source group 202 are powered in the base pattern depicted in FIG. 9; clitoral vibrator 304 operates in a continuous LOW power state; and the blue, red and infrared LEDs of clitoral light source group 302 are also powered in the base pattern depicted in FIG. 9.

Continuing to discuss now the exemplary mode of operation described above, when the invention is in the base operating mode, pressing third depressible control button 407 alone causes controller 501 to command vaginal vibrator 204 and clitoral vibrator 304 to increase intensity by commanding a higher duty cycle as hereinbefore described, and pressing third depressible control button 407 again causes controller 501 to command vaginal vibrator 204 and clitoral vibrator 304 to further increase intensity. Each press shall result in an increase of $\frac{1}{6}^{th}$ of intensity range until maximum intensity is reached. Thus, in the exemplary base operating mode described herein, pressing third depressible control button 407 generally results in an increase in perceived vibration intensity to the user. Likewise, when the invention is in the base operating mode, pressing first depressible control button 405 alone causes controller 501 to command vaginal vibrator 204 and clitoral vibrator 304 to decrease intensity by commanding a lower duty cycle. Thus, in the exemplary base operating mode described herein, pressing first depressible control button 405 generally results in a decrease in perceived vibration intensity to the user. In this manner the user may select a desired intensity of vibration. Any number of vibration intensity levels may be programmed into controller 501 and memory 502.

Figure 9:
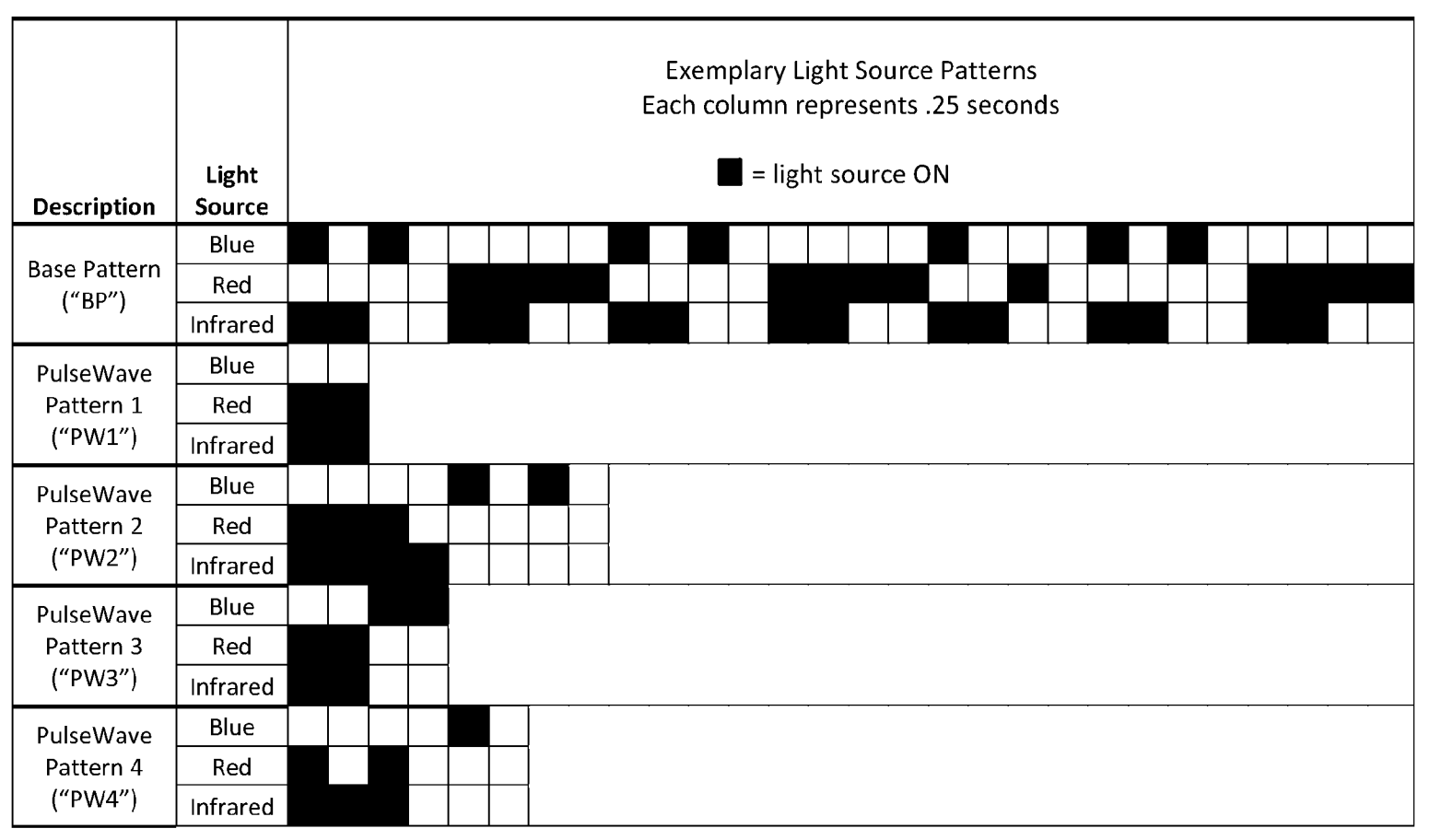

Continuing to discuss now the exemplary mode of operation described above, when the invention is in the base operating mode, depressing and holding fifth depressible control button 409 may cause controller 501 to command vaginal vibrator 204 and clitoral vibrator 304 and the light sources of light source groups 202 and 302 to cycle through a series of programmed states which may include, for the vibrators: continuous ON in LOW power state, continuous OFF state, pulsed ON and OFF in both in-phase and out-of-phase states; and sinusoidal in both in-phase and out-of-phase states; and, for the light source groups 202 and 302: continuous ON state for all light sources, continuous OFF state for all light sources, the base pattern and other patterns shown in FIG. 9. The invention may cycle through each of these states in series as programmed into controller 501 and memory 502, taking, for example, approximately seven minutes to complete the cycle. The length of time of the cycle may be programmable, as is the sequencing and description of the states of the vibrators and light sources. Pressing any button during the cycle may return the invention to the base operating mode. A exemplary preferred program of light energy and motor stimulation is shown in FIGS. 9 and 10.

Continuing to discuss now the exemplary mode of operation described above, when the invention is in the base operating mode, pressing first depressible control button 405 and third depressible control button 407 simultaneously for three seconds may cause controller 501 to command vaginal vibrator 204 and clitoral vibrator 304 to an OFF state, and likewise commend all light sources of vaginal light source group 202 and clitoral light source group 302 to an OFF state.

It is to be noted that pulse width of the PWM drive signal to the vibrators of the invention may be varied independently of one another by controller 501 in any pattern desired such as, for example, continuous ON, continuous OFF, sinusoidal, square, ramped, and so on, by modulation of the pulse width of the PWM drive signal. Also, as herein used, "in-phase" means that the PWM signal to vaginal vibrator 204 and clitoral vibrator 304 are of like waveform with substantially identical timing. "Out-of-phase" means that the PWM signal to vaginal vibrator 204 and clitoral vibrator 304 are of like waveform but are substantially 180 degrees out of phase. It is further to be noted that the PWM drive signals provided to vaginal vibrator 204 and clitoral vibrator 304 are provided independently of one another. Thus, the PWM waveforms to vaginal vibrator 204 and clitoral vibrator 304 may take independently take any shape desired.

Referring now to FIG. 9, and keeping with the exemplary embodiment used in the above description of an exemplary mode of operation of the invention, the timing of various exemplary light source patterns are depicted to provide further detail as to the variety of patterns of light energy emission that may be programmed into controller 501 and memory 502. It can readily be seen that the pattern defined as Base Pattern, for example, causes the blue and infrared LEDs of a light source group to turn ON for 0.25 seconds, after which the blue LED turns OFF for 0.25 seconds while the infrared LED remains ON, and so on. In this manner any number of light source patterns may be defined and programmed into controller 501. Once the patterns have run their course they may repeat. In the examples shown in FIG. 9, five light source patterns are depicted for the exemplary case in which a light source group comprises blue LEDs, red LEDs, and infrared LEDs, in keeping with the exemplary embodiment used in the description of the exemplary mode of operation above. The five exemplary patterns depicted in FIG. 9 are Base Pattern ("BP"); PulseWave Pattern 1 ("PW1"); PulseWave Pattern 2 ("PW2"); PulseWave Pattern 3 ("PW3"); and PulseWave Pattern 4 ("PW4"). Once such patterns are defined and programmed into controller 501 and memory 502, they may be used in combination with vibrator patterns also programmed into controller 501 and memory 502 in order to define further exemplary modes of operation of the invention, as discussed below.

Referring next to FIG. 10, and keeping with the exemplary embodiment used in the above description of an exemplary mode of operation of the invention, the timing of various exemplary vibrator patterns are depicted to provide further detail as to the variety of patterns of vibration that may be programmed into controller 501 and memory 502. It can readily be seen that the pattern defined as Constant, for example, causes the vibrators to operate continuously at a constant power level. In this manner any number of vibration patterns may be defined and programmed into controller 501 and memory 502. Once the patterns have run their course they may repeat. In the examples shown in FIG. 10, six vibration patterns are depicted for the exemplary case in which the invention comprises a vaginal vibrator 204 and a clitoral vibrator 304, in keeping with the exemplary embodiment used in the description of the exemplary mode of operation above. The six exemplary vibrator patterns depicted in FIG. 10 are constant ("C"), In Phase Pulse ("IPP"), Out of Phase Pulse ("OPP"), In Phase Wave ("IPW"), Out of Phase Wave ("OPW"), and Fast Pulse ("FP"). Once such patterns are defined and programmed into controller 501 and memory 502, they may be used in combination with light source patterns also programmed into controller 501 and memory 502 in order to define further exemplary modes of operation of the invention, as discussed below.

Referring now to FIG. 11, another exemplary mode of operation is defined, consistent with the above description of an exemplary mode of operation, for the exemplary embodiment of the invention which both clitoral and vaginal light source groups 302 and 202, respectively, comprise blue LED light sources, red LED light sources, and infrared LED light sources and in which vaginal finger 200 and clitoral finger 300 comprise a vibrator. It is readily seen from FIG. 11 that in the first sixty seconds, both vaginal vibrator 204 and clitoral vibrator 304 operate in a continuous mode at LOW power while vaginal light source group 202 and clitoral light source group 302 operate in pattern PW1 as was defined in FIG. 9.

After the first sixty seconds and until 180 seconds have elapsed, both vaginal vibrator 204 and clitoral vibrator 304 operate in a continuous mode at MEDIUM power while vaginal light source group 202 and clitoral light source group 302 operate in pattern PW2 as was defined in FIG. 9. After 180 seconds have elapsed and until 300 seconds have elapsed, both vaginal vibrator 204 and clitoral vibrator 304 operate in a continuous mode at MEDIUM power while vaginal light source group 202 and clitoral light source group 302 operate in pattern PW3 as was defined in FIG. 9. After 300 seconds have elapsed and until 480 seconds have elapsed, both vaginal vibrator 204 and clitoral vibrator 304 operate in a continuous mode at HIGH power while vaginal light source group 202 and clitoral light source group 302 operate in pattern PW4 as was defined in FIG. 9. After 480 seconds have elapsed, both vaginal vibrator 204 and clitoral vibrator 304 operate in a continuous mode at MEDIUM power while vaginal light source group and clitoral light source group operate in pattern PW4 as was defined in FIG. 9. In this exemplary mode of operation, the invention will continue to run in this state until the user powers the invention to an OFF state as defined above, or presses any button which returns the invention to base motor and light patterns, in an alternate embodiment, the invention may time out after a set period of time.

It is not necessary that the vibrators and light sources of the invention operation in the same pattern at the same time; in fact, the great majority of vibrator and light source patterns may comprise different patterns for the vibrators and light sources of the invention as they are all controlled individually by controller 501. It is thus readily seen that any pattern of operation of vibration and light source patterns may be programmed into controller 501 and memory 502.

Although a detailed description of the preferred and alternate embodiments as provided in the description and drawings contains many specifics for the purposes of illustration, a person of ordinary skill in the art will appreciate that many variations and alterations to the details are within the scope of the invention. Accordingly, the preferred and alternate embodiments of the invention are set forth without any loss of generality to, and without imposing limitations upon, the claimed invention. Thus the scope of the invention should be determined by the appended claims and their legal equivalents, and not merely by the preferred examples or embodiments given.

INDUSTRIAL APPLICABILITY

The improved sexual stimulation device using light therapy and vibration of the invention presents a novel and unique structure, not heretofore found in the prior art, which combines vibrational energy and light energy to improve vaginal and clitoral blood flow such that the experience of a user of the invention is enhanced over the devices of the prior art. Additional benefits may include improved blood supply to genitals and a decrease in both pathogenic bacteria and fungi. The improved sexual stimulation device using light therapy and vibration of the invention has direct applicability to the adult toy industry and related markets, and represents a significant improvement in the state of the art of adult pleasure objects.

What is claimed is:

1. A sexual stimulation device, comprising:
a vaginal finger portion having a first mechanical stimulation means and a first light source group disposed therein, wherein said first light source group comprises at least one light source adapted to emit vaginal light energy from said vaginal finger portion;
a handle portion having a power source, a keypad, and a controller disposed therein; and
a clitoral finger portion having a second mechanical stimulation means and a second light source group disposed therein, wherein said second light source group comprises at least one light source adapted to emit clitoral light energy from said clitoral finger portion;
wherein said vaginal finger portion, said clitoral finger portion and said handle portion are in communication forming a structure configured such that when said vaginal finger portion is slidingly engaged with and inserted into the vagina of a user said handle portion remains outside a user's vagina; and
wherein said controller is in electrical communication with said first mechanical stimulation means, said second mechanical stimulation means, said first light source group, said second light source group, said keypad and said power source, and wherein said controller is adapted to receive power from said power source and to receive commands by user operation of said keypad, and wherein said controller is further adapted to control operation of said first mechanical stimulation means, said second mechanical stimulation means, said at least one light source of said first light source group and said at least one light source of said second light source group in response to commands received by a user through said keypad; and
wherein said vaginal finger portion is defined as an elongated shape having a longitudinal axis and having a first end and a second end wherein said vaginal finger portion first end is adapted to be inserted into the vagina of a user and said vaginal finger portion second end is in communication with said handle, and wherein said clitoral finger portion is defined as an elongated shape having a longitudinal axis and having a first end and a second end, wherein clitoral finger portion said second end is in communication with said handle;
wherein said longitudinal axis of said vaginal finger portion and said longitudinal axis of said clitoral finger portion are parallel; and
wherein said clitoral finger portion is configured such that when said vaginal finger portion is slidingly engaged with and inserted into the vagina of a user, said second mechanical stimulation means engages a user on or near a user's clitoris while said handle portion remains outside a user's vagina.

2. The sexual stimulation device of claim 1, wherein said first light source group is oriented such that said vaginal light energy impacts a user's body in an area of the Graffenberg Spot of a user when said vaginal finger portion is slidingly engaged with and inserted into the vagina of a user and when said second mechanical stimulation means engages a user on or near a user's clitoris.

3. The sexual stimulation device of claim 2, wherein said second light source group is oriented such that said clitoral light energy impacts a user's body in the area of the clitoris of a user when said vaginal finger portion is slidingly engaged with and inserted into the vagina of a user and said vaginal light energy is impacting a user's body on said area of the Graffenberg Spot.

4. The sexual stimulation device of claim 3, wherein said vaginal light energy emitted by said first light source group is between 400 nm and 1000 nm in wavelength, and wherein said clitoral light energy emitted by said second light source group is also between 400 nm and 1000 nm in wavelength.

5. The sexual stimulation device of claim 4, wherein said power source is a battery selected from the group consisting of a replaceable battery and a rechargeable battery.

6. The sexual stimulation device of claim 4, wherein said first mechanical stimulation means and said second mechanical stimulation means are vibrators.

7. The sexual stimulation device of claim 6, wherein said vibrators are offset vibrator motors.

8. The sexual stimulation device of claim 7, wherein said first and second vibrators are offset vibrator motors adapted to operate at a vibration rate of between 5,000 and 25,000 rotations per minute.

9. The sexual stimulation device of claim 3, wherein said first light source group is further defined as comprising a first light source emitting light energy with wavelength between 400 nm and 1000 nm and a second light source emitting light energy with wavelength between 400 nm and 1000 nm, and wherein said second light source group is further defined as comprising a third light source emitting light energy with wavelength between 400 nm and 1000 nm and a fourth light source emitting light energy with wavelength between 400 nm and 1000 nm.

10. The sexual stimulation device of claim 9, wherein said power source is a battery selected from the group consisting of a replaceable battery and a rechargeable battery.

11. The sexual stimulation device of claim 9, wherein said first mechanical stimulation means and said second mechanical stimulation means are offset vibrator motors.

12. The sexual stimulation device of claim 11, wherein said first and second vibrators are offset vibrator motors adapted to operate at a vibration rate of between 5,000 and 25,000 rotations per minute.

13. The sexual stimulation device of claim 9 wherein said first, second, third, and fourth light sources are further defined as light emitting diodes.

14. The sexual stimulation device of claim 13 wherein said first, second, third and fourth light sources are further characterized as having an output power of at least 300 millicandelas with a half-power output angle of +/−60 degrees.

15. The sexual stimulation device of claim 3, wherein said first light source group is further defined as comprising a first light source emitting light energy with wavelength between 400 nm and 515 nm, a second light source emitting light energy with wavelength between 610 nm and 640 nm, and a third light source emitting infrared light energy with wavelength between 820 nm to 880 nm, and wherein said second light source group is further defined as comprising a fourth light source emitting light energy with wavelength between 400 nm and 515 nm, a fifth light source emitting light energy with wavelength between 610 nm and 640 nm, and a sixth light source emitting infrared light energy with wavelength between 820 nm and 880 nm.

16. The sexual stimulation device of claim 15, wherein said power source is a battery selected from the group consisting of a replaceable battery and a rechargeable battery.

17. The sexual stimulation device of claim 15, wherein said first mechanical stimulation means and said second mechanical stimulation means are offset vibrator motors.

18. The sexual stimulation device of claim 17, wherein said first and second vibrators are offset vibrator motors adapted to operate at a vibration rate of between 5,000 and 25,000 rotations per minute.

19. The sexual stimulation device of claim 15, wherein said first, second, third, fourth, fifth and sixth light sources are further defined as light emitting diodes.

20. The sexual stimulation device of claim 19, wherein said first, second, fourth and fifth light sources are further characterized as having an output power of at least 300 millicandelas with a half-power output angle of +/−60 degrees; and said third and sixth light sources are further characterized as having output radiant flux of at least 300 mW peak with a half-power output angle of +/−60 degrees.

21. The sexual stimulation device of claim 3 further defined as having a memory in communication with said controller, said memory adapted to store at least one pre-programmed mode controlling the operation of said first mechanical stimulation means, said second mechanical stimulation means, said at least one light source of said first light source group, and said at least one light source of said second light source group.

22. The sexual stimulation device of claim 21, wherein said controller is adapted to receive user commands via said keypad by selecting a mode of operation from said at least one pre-programmed mode of operation stored in said memory.

23. The sexual stimulation device of claim 22, wherein said at least one pre-programmed mode of operation comprises a mode of operation in which said first mechanical stimulation means operates with an intensity modulated sinusoidally and having a first sinusoidal period, and in which said second mechanical stimulation means operates with an intensity modulated sinusoidally and having a second sinusoidal period.

24. The sexual stimulation device of claim 23, wherein said first sinusoidal period and said second sinusoidal period are in phase.

25. The sexual stimulation device of claim 24, wherein said at least one pre-programmed mode of operation further comprises a mode of operation in which said at least one light source of said first light source group and said at least one light source of said second light source group are independently powered to an ON state for a period of between 0.25 to 1.00 seconds followed by an OFF state for a period of between 0.25 to 1.25 seconds.

26. The sexual stimulation device of claim 23, wherein said first sinusoidal period and said second sinusoidal period are out of phase.

27. The sexual stimulation device of claim 26, wherein said at least one pre-programmed mode further comprises a mode of operation in which said at least one light source of said first light source group and said at least one light source of said second light source group are independently powered to an ON state for a period of between 0.25 to 1.00 seconds followed by an OFF state for a period of between 0.25 to 1.25 seconds.

28. The sexual stimulation device of claim 23, wherein said at least one pre-programmed mode further comprises a mode of operation in which said at least one light source of said first light source group and said at least one light source of said second light source group are independently powered to an ON state for a period of between 0.25 to 1.00 seconds followed by an OFF state for a period of between 0.25 to 1.25 seconds.

* * * * *